(12) United States Patent
Pawluczyk et al.

(10) Patent No.: US 6,741,875 B1
(45) Date of Patent: May 25, 2004

(54) METHOD FOR DETERMINATION OF ANALYTES USING NEAR INFRARED, ADJACENT VISIBLE SPECTRUM AND AN ARRAY OF LONGER NEAR INFRARED WAVELENGTHS

(75) Inventors: Romauld Pawluczyk, Conestogo (CA); Thomas Scecina, Medfield, MA (US); Theodore E. Cadell, Conestogo (CA)

(73) Assignee: CME Telemetrix Inc., Waterloo (CA)

( * ) Notice: Subject to any disclaimer, the term of this patent is extended or adjusted under 35 U.S.C. 154(b) by 0 days.

(21) Appl. No.: 10/070,189

(22) PCT Filed: Aug. 31, 2000

(86) PCT No.: PCT/CA00/01003

§ 371 (c)(1),
(2), (4) Date: Jun. 3, 2002

(87) PCT Pub. No.: WO01/16578

PCT Pub. Date: Mar. 8, 2001

Related U.S. Application Data

(60) Provisional application No. 60/151,685, filed on Aug. 31, 1999.

(51) Int. Cl.[7] .................. A61B 5/00; G01J 3/28

(52) U.S. Cl. .............. 600/310; 600/322; 356/328; 250/339.05; 250/339.07; 250/341.8

(58) Field of Search .................. 600/310, 316, 600/322, 323, 473; 356/39, 300, 319, 320, 326, 328; 250/339.01, 339.02, 339.05, 339.06, 339.07, 339.11, 339.12, 340, 341.1, 341.2, 341.8

(56) References Cited

U.S. PATENT DOCUMENTS 5,830,132 A * 11/1998 Robinson .................. 600/310

* cited by examiner

*Primary Examiner*—Eric F. Winakur
(74) *Attorney, Agent, or Firm*—Hovey Williams LLP

(57) ABSTRACT

Described is a method which uses spectral data simultaneously collected in a continuous array of discrete wavelength points of the visible spectrum adjacent to the infrared and near infrared part of the light spectrum. The spectral data is collected using a number of detectors with different sensitivity ranges. Some detectors may be sensitive to visible and possibly, to part of the near infrared portion of radiation. Spectral data from die infrared spectrum is collected with the infrared detectors, and are in some embodiments insensitive to the visible links.

24 Claims, 2 Drawing Sheets

METHOD FOR DETERMINATION OF ANALYTES USING NEAR INFRARED, ADJACENT VISIBLE SPECTRUM AND AN ARRAY OF LONGER NEAR INFRARED WAVELENGTHS

This application claims the benefit of provisional application Ser. No. 60/151,685, filed Aug. 31, 1999.

FIELD OF INVENTION

This invention relates to a device and method for determining and monitoring concentration levels of one or more constituents within a varying in time, complex multi component structure, (for example blood constituents in blood sample, tissue or body parts) or, in particular, blood and tissue constituents in living subjects such as humans or animals.

BACKGROUND OF INVENTION

The application of spectroscopy for chemical analysis is well known. For many years, however, it was mainly used for atomic analysis because sufficiently sensitive detectors did not exist for infrared, where information on vibration states of the molecules (especially those of organic origin) is located. Advances in technology of IR detectors have dramatically changed the situation and presently a large number of detectors, instruments and methods exist for such applications. This has also opened the way for new applications, but has imposed new requirements on the technology. One of the most important applications is a noninvasive analysis of chemical compositions of living subjects.

It is generally appreciated that light in spectral range 500 nm to 770 nm belongs to the visible part of the spectrum but, since it does not cover whole visible range and it is directly adjacent to the infrared part of the spectrum, herein it is referred to as adjacent visible (AV). It is widely accepted that of the infrared part of the electromagnetic spectrum (IR) is divided into the near infrared (NIR), which expands beyond the visible to about 2700 nm, the middle infrared radiation (MIR), which expands beyond the NIR range and a further expanding far infrared range (FIR). There are some photodetectors (mainly silicon) whose sensitivity covers the visible part of spectrum and initial part of NIR. Therefore, part of visible range adjacent to NIR and part of NIR adjacent to visible will be referred here as AV/NIR, while the remaining part of NIR range will be referred to as the "longer wavelength NIR region" or "LWNIR".

Non-Invasive Techniques

Previous devices for non-invasively monitoring concentration of blood constituents of a patient are known. Usually, a sensor is used to externally measure either the concentration of the constituents in gases emitted by the body or contained in the perspiration, or the concentration of the constituents contained in body fluids such as tears, saliva, or urine. Alternatively, the blood constituents are identified by measurement of attenuation of some radiation passed through a part of a patient's body such as an earlobe, a finger or skin. In majority cases, radiation is measured at one, two or limited number of relatively narrow spectral bands obtained from separate, narrow band light sources (see for example U.S. Pat. No. 4,655,225; U.S. Pat. No. 4,883,953; and U.S. Pat. No. 4,882,492). Some of these devices perform measurements at limited number relatively narrow spectral bands consecutively selected from spectrally broad light by a set of exchangeable narrow-band spectral filters. Analysis of absolute and relative changes in light intensity at these bands under certain conditions may provide important information on body constituents. Exchange of the filters and time required for their stabilization to obtain precise measurement, very often significantly increase duration of the measurement process and as a result, the measurement in different bands are taken with significant time delays. Because of physiological variability of physical state of the alive person, this leads to situation when measurements at different wavelengths are taken under changed physical conditions of the body, making impossible to measure the constituents of the body. Another source of the error in the systems with limited number of discrete spectral bands is wavelength shift of the selected bands from measurement to the measurement and from instrument to the instrument. There are some medical and other applications when these two sources of the error make measurement of constituents impossible. In such a case it becomes important to make the measurement in whole spectrum virtually simultaneously and to preserve as complete as possible information on whole spectrum. This is achieved applying other techniques, which measure either a full spectrum of light interacting with sample, with a large number (for example, 128 or 256) of wavelengths in a specific range and those that measure a limited number of wavelengths. Those that measure full spectra typically use the wavelengths in the AV/NIR range (see for examples U.S. Pat. No. 5,361,758 and U.S. Pat. No. 4,975,581), where arrays of the photodetectors, produced with application of well established silicon technology, have been available for long time for simultaneous registration of the spectra in large number of discrete points. There are several advantages in measurement of whole spectrum. One of them consists in that the spectra provide information about the desired analyte as well as information about interfering substances (e.g., other analytes) and effects (e.g., light scattering). The second advantage is capability to register a complete information on spectrum even if it is shifted due to temperature changes of sample. Finally, the third advantage is that even if the instrument loses wavelength calibration, whole information is still preserved in the spectrum and can be easily extracted once new wavelength calibration data is available. In some cases, however, there is not enough information available in the above range or available information is insufficient for precise measurement of body constituents and additional information outside the above mentioned spectral range (usually at longer wavelengths) is required.

In some cases, the methods that take measurements at limited number of wavelengths only within the 1100 to 1700 nm region can be sufficient, because of the sharper analyte spectra that exist in this region. In majority cases, however, while they provide information relating to the analyte of interest, there is not enough independent information on other analytes whose absorption spectra interferes with that of the desired analyte. In some cases additional information obtained in earlier mentioned spectral range 580 nm to 1100 nm helps to eliminate ambiguity introduced by interfering analytes. It is clear that if the sample demonstrates a temporal variability, a simultaneous measurement in whole spectral range of the interest is preferred, to eliminate possible errors caused by changes in the sample.

Furthermore, as in earlier discussed cases for shorter spectral range, spectral measurement in limited number of points within 1100 nm to 1700 nm spectral range in some cases may not be sufficient for recognition of desired analyte. In addition, the measurements usually are very sensitive to both: variations of spectral position of the selected points and width and shape of spectral bands measured at those points. Thus, the methods when measurement in different parts of spectrum are taken at different time, or from different part of samples or within limited number of points may not be sufficient for precise analysis of constituents of the samples and more advanced instruments are required. The way to eliminate these limitations and provide instrument suitable for such measurements is given it this invention. Overall, previous non-invasive devices and techniques have not been sufficiently accurate to be used in place of invasive techniques in the measurement of blood constituent concentration in patients. Some of them have been designed to measure one component only and physical changes to the instrument have to be applied to adapt them to measurement of different components. For some devices it takes unreasonably long time to produce a results; or, some other cannot produce results in an easy-to-use form; or, they cannot measure concentration of two or more constituents simultaneously. Obviously, if the device gives an inaccurate reading, disastrous results could occur for the patient using the device to calculate, for example, dosages for insulin administration.

It has been recognized that simultaneous spectrum collection is possible only by applying a large number of photodetectors. Technically this is brought about by spatial dispersion of radiation, composed of different wavelengths, by means of a dispersing device (diffraction grating, for example) and registration of its intensity with an array of photodetectors. In such cases, the signal registered by each detector of the array can be read virtually simultaneously. This technique has been recognized and many spectrometers with an array of photodetectors are available on the market. Unfortunately, the available arrays systems have various limitations, therefore, the capabilities of such spectrometers are limited.

The most important limitation for each array is its sensitivity range, which is determined by the material used to produce an array. The sensitivity range determines in what spectral range the instrument built with an application of a particular array can work. Grating spectrometers designed with the application of arrays of photodetectors have further intrinsic limitations, which put even stronger constrains on the performance of the instruments. One such constraint is the existence of additional diffraction orders in light diffracted by a grating. The existence of the second order imposes the condition that the spectral range of an array-based instrument cannot be wider than one octave, unless a special filter is placed in front of the array. Production of such filters is not easy, hence, instruments are built to cover less than one octave and a cut-off filter, eliminating radiation with shorter wavelengths is normally used to eliminate the impact of that order. As a result, the spectral range of existing array-based instruments is such that the longest measured wavelength of analyzed light is always smaller than the doubled length of the shortest wavelength analyzed by the spectrometer Finally, since the number of elements in an array and length of an array are limited, very often it is impossible to achieve high resolution even in that limited spectral range. As a result, the performance of array-based instruments is a compromise between such factors and consequently spectrometers very often cannot provide information needed for particular applications. If, in addition, these applications require simultaneous registration of the wider spectrum (as, for example, non-invasive in-vivo diagnostic), the measurement problem remains unsolved.

SUMMARY OF THE INVENTION

While for some applications relatively simple instruments, measuring of infrared radiation at one or small number of wavelengths are sufficient, it was discovered that for more demanding applications, such as, for example, glucose concentration in blood in a human body, significantly more advanced instruments are required. In particular it has been found that for such applications it is important to collect data in a wide spectral range covering at least part of near infrared and adjacent to it visible part of the spectrum. It has been also discovered that for living subject it is crucial that information is collected simultaneously in whole spectral -range of the interest, otherwise physiological changes in the organism during measurement may significantly contribute to the measurement error. Finally, it has been found that because of dependence of the molecular vibration spectrum on temperature it is important to have as complete information on the spectrum as possible. Therefore a need has arisen to build a spectroscopic system able to simultaneously collect information in as wide spectrum as possible. This approach excludes techniques when a spectrum of light is collected with the application of any scanning instrument like those with rotated gratings or Fourier transform spectrometers.

Accordingly, the present invention provides a method for monitoring the concentration level of a particular constituent in a sample or, alternatively, of measuring the concentration level of one or more different constituents using a non-invasive device with higher precision and in a short period of time, through simultaneous measurement of light signal in several different spectral ranges using separate array-based spectrometers.

The present inventors have determined that analyte measurement accuracy with spectral devices measuring full spectra absorption/reflectance in the AV/NIR region, is enhanced by adding to such measurement, measurements from one or more arrays of wavelength in the infrared region In its broad aspect the present invention provides a method for monitoring the concentration level of a constituent in sample comprising placing the sample in a non-invasive device capable of emitting radiation; directing the radiation onto the sample; measuring radiation collected from the sample; calculating the concentration level based on the measured radiation wherein the radiation directed onto the tissue and collected from the tissue is of the wavelengths starting at 500 nm and expanding into AV/NIR range, and wavelengths in the LIR range possible from 1100 to 1700 nm.

According to one embodiment, the present invention provides a method for measuring concentration levels of blood constituents within a living subject such as humans or animals, wherein, a polychromatic light source or other single or multiplicity of radiation sources are used that emit a broad spectrum of light in the required range. A number of spectrum analyzing systems containing photodetector arrays, possible sensitive in different spectral ranges provide sensitivity and resolution over portions of the range of the interest, preferably one from 500–1100 nm and one from 900–1700 nm and further spectral ranges. The method comprises the steps of:

directing light at a continuum wavelengths (whether from one or more sources) simultaneously onto a sample or a part of a subject;

collecting the continuum of light after the light has been directed onto and interacted with the sample or the part;

dividing of collected light into at least two parts separately directed to the corresponding number of spectrum analyzing systems, at least one for AV/NIR and at least another one for WNIR, forming of each part of light into a light beam, suitable for simultaneous analysis of corresponding spectral content of each part, preferably by means of a dispersing element, preferable diffraction grating, spatially dispersing a portion of the continuum of light predestined for analysis with separate spectrum analyzing systems into a dispersed spectrum of component wavelengths in each selected part, forming of dispersed light in each part into light beam suitable for detection with a suitable array of photodetectors, the arrays of the photodetectors taking measurement of dispersed light in selected part or whole AV/NIR spectral range and at least one or more arrays applied for measurements of at least selected part or whole LWNIR spectral range.

Preferably these measurements are taken simultaneously or sequentially, or in any combination thereof. The measurement results are transferred to a microprocessor, and the concentration level of said at least one constituent of the sample, in particular of said blood or tissue is calculated and a result of each concentration level is produced.

According to another embodiment of the invention, there is provided a non-invasive device measuring concentration levels of constituents occurring in the sample in particular in blood and tissue in a subject such as a human or animal uses one or more radiation sources. The broad spectrum of light in the adjacent visible spectrum and near infrared range provided by the radiation or light source(s) is/are powered by one or a required number of stabilized power sources. The device (or devices) has a receptor shaped so that a sample or a part of the subject can be placed in contact with the receptor. The receptor has means for eliminating extraneous light and is located relative to the light source (or sources) so that when a sample or body part (or tissue) is placed in contact with the receptor, the source(s) can be activated and light with continuum of wavelengths, is directed onto the part. The device is equipped with means for collecting light in the AV/NIR and LWNIR spectral regions after the light has been directed onto the sample or the part. There are also means for dispersing the collected light over said broad spectrum into a dispersed spectrum of component wavelengths and means for taking measurements of a light signal at many different wavelengths in the AV/NIR and LWNIR regions simultaneously or sequentially. There are also means for transforming results of these measurements over the dispersed spectrum into the concentration of at least one constituent by using a calibration equation for the at least one constituent. There are also means for determining the concentration level of the at least one constituent of said blood or tissue and then producing a result for each concentration level determined.

According to one embodiment of the present invention there is provided a method for determining a concentration of a constituent in a sample comprising the steps of:

irradiating the sample with a continuum of wavelengths from the adjacent visible and near infrared (AV/NIR) region;

collecting radiation after the radiation has been directed onto the part;

dispersing the continuum of collected radiation into a dispersed spectrum of component wavelengths onto a detector, the detector taking measurements of at least one of transmitted or reflected radiation from the collected radiation; and transferring the measurements to a processor;

irradiating the sample with a continuum of wavelengths in the longer wavelength near infrared (LWNIR) region; detecting one or more bands of radiation after the radiation has been directed onto the sample with a detector, the detector taking measurements of at least one of transmitted or reflected radiation; and transferring the measurements to a processor;

based on the measurements and one or more calibration algorithms, the processor calculating the concentration of said constituent in said sample, preferably one or more separate energy sources are used to provide radiation.

According to another embodiment of the method of the invention the detector of the AV/NIR is one or more spectral instruments with an array of silicon detectors and the detector of LWNIR is one or more spectral instruments with a separate array of infrared sensitive detectors for each band of radiation.

According to yet another embodiment the detector of the AV/NIR is one or more spectral instruments with an array of silicon detectors and the detector of LWNIR is one or more spectral instruments with an array of infrared sensitive detectors and measurements for each band of radiation are taken from appropriate members of the array of infrared sensitive detectors, preferably the infrared sensitive detectors are InGaAs detectors.

According to another embodiment the spectrometers with silicon detectors arrays register light in the all of the visible, visible/infrared and adjacent to visible infrared ranges within the spectral sensitivity range of the detectors, and preferably the spectrometers with infrared sensitive detectors register light in the separate infrared ranges within their spectral sensitivity range.

According to another embodiment of the method all detectors register light in their respectable sensitivity ranges virtually simultaneously.

In another aspect of the present invention there is provided a method for determining a concentration of a constituent in a sample comprising the steps of:

irradiating the sample with a continuum of wavelengths from the AV/NIR region;

collecting radiation after the radiation has been directed onto the part;

dispersing the continuum of collected radiation into a dispersed spectrum of component wavelengths onto a detector, the detector taking measurements of at least one of transmitted or reflected radiation from the collected radiation; and transferring the measurements to a processor;

irradiating the sample with one or more bands of wavelengths in the LWNIR region; detecting the one or more bands of radiation after the radiation has been directed onto the sample with a detector, the detector taking measurements of at least one of transmitted or reflected radiation; and transferring the measurements to a processor;

based on the measurements and one or more calibration algorithms, the processor calculating the concentration of said constituent in said sample, preferably one or more separate energy sources are used to provide radiation.

According to another embodiment of the method of the invention the detector of the AV/NIR is one or more spectral instruments with an array of silicon detectors and the detector of LWNIR is one or more spectral instruments with a separate array of infrared sensitive detectors for each band of radiation.

According to yet another embodiment the detector of the AV/NIR is one or more spectral instruments with an array of silicon detectors and the detector of LWNIR is one or more spectral instruments with an array of infrared sensitive detectors and measurements for each band of radiation are taken from appropriate members of the array of infrared sensitive detectors, preferably the infrared sensitive detectors are InGaAs detectors.

According to another embodiment the spectrometers with silicon detectors arrays register light in the all of the visible, visible/infrared and adjacent to visible infrared ranges within the spectral sensitivity range of the detectors, and preferably the spectrometers with infrared sensitive detectors register light in the separate infrared ranges within their spectral sensitivity range.

According to another embodiment of the method all detectors register light in their respectable sensitivity ranges virtually simultaneously.

In yet another aspect of the present invention there is provided a method for determining a concentration of a constituent in a sample comprising the steps of:

irradiating the sample with a continuum of wavelengths from the AV/NIR region;

collecting radiation after the radiation has been directed onto the part;

dispersing the continuum of collected radiation into a dispersed spectrum of component wavelengths onto a detector, the detector taking measurements of at least one of transmitted or reflected radiation from the collected radiation; and transferring the measurements to a processor;

irradiating the sample with a continuum of wavelengths from the LWNIR region; collecting radiation after the radiation has been directed onto the part;

dispersing the continuum of collected radiation into a dispersed spectrum of bands of radiation onto a detector, the detector taking measurements of at least one of transmitted or reflected radiation; and transferring the measurements to a processor;

based on the measurements and one or more calibration algorithms, the processor calculating the concentration of said constituent in said sample, preferably one or more separate energy sources are used to provide radiation.

According to another embodiment of the method of the invention the detector of the AV/NIR is one or more spectral instruments with an array of silicon detectors and the detector of LWNIR is one or more spectral instruments with a separate array of infrared sensitive detectors for each band of radiation.

According to yet another embodiment the detector of the AV/NIR is one or more spectral instruments with an array of silicon detectors and the detector of LWNIR is one or more spectral instruments with an array of infrared sensitive detectors and measurements for each band of radiation are taken from appropriate members of the array of infrared sensitive detectors, preferably the infrared sensitive detectors are InGaAs detectors.

According to another embodiment the spectrometers with silicon detectors arrays register light in the all of the visible, visible/infrared and adjacent to visible infrared ranges within the spectral sensitivity range of the detectors, and preferably the spectrometers with infrared sensitive detectors register light in the separate infrared ranges within their spectral sensitivity range.

According to another embodiment of the method all detectors register light in their respectable sensitivity ranges virtually simultaneously.

In accordance with a preferred embodiment of any of the forgoing methods the sample is a finger of a subject.

Other features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawing in which.

DETAILED DESCRIPTION OF THE INVENTION

As used herein "concentration" or "concentration level" means the amount or quantity of a constituent in a solution whether the solution is in vitro or in vivo.

As used herein, "constituent" means a substance, or analyte found in a tissue and includes carbohydrates such as for example glucose, bilirubin, a protein, for examples albumin or, hemoglobin.

As used herein, "in a solution" means in a liquid environment such as, for examples interstitial, or other bodily fluid As used herein, "tissue" means any tissue of the body of a subject including for example, blood, extracellular spaces, and can mean the entire composition of a body part such as a finger or ear lobe.

As used herein "subject" means any member of the animal kingdom including, preferably, humans.

As noted previously, light in spectral range 500 nm to 770 nm is referred to herein as adjacent visible (AV). As used herein, the infrared part of the electromagnetic spectrum (IR) is divided into the near infrared (NIR), which expands beyond the visible to about 2700 nm, the middle infrared radiation (MIR), which expands beyond the NIR range and a further expanding far infrared range (FIR). Also, part of visible range adjacent to NIR and part of NIR adjacent to visible will be referred here as AV/NIR, while the remaining part of NIR range will be referred to as the "longer wavelength NIR region" or "LWNIR".

According to a preferred embodiment, in each case, it is assumed that measurement of the light intensity at any given spectral band with given central wavelengths is at a sufficiently high signal to noise ratio in order to achieve the desired results.

As discussed above, the present inventors have determined that significant improvement of the ability to measure analytes in various samples (in tissue in particular) using a non-invasive spectral device can be achieved by adding; it is only necessary to add one or more arrays of wavelength measurements in the LWNIR or IR region to a full spectra absorption measurement in the 500 to 1100 nm region to gain a significant improvement in analyte measurement accuracy. In particular analyte measurement accuracy achieved through previous methods is enhanced by adding a full spectra absorption measurement in the 1100 to 1300 nm (the "First region") and/or by adding a full spectra absorption measurement in the 1590 to 1700 nm (the "Second region") region to a full spectra absorption measurement in the 500 to 1100 nm region, preferably in the AV/NIR region, more preferably the addition of the First region to the Second region is performed. The result provides a significant improvement in analyte measurement accuracy. It will be readily appreciated that the method indudes addition of measurements of full spectra absorption from other regions or whole range in the LWNIR or IR.

Figure 1:
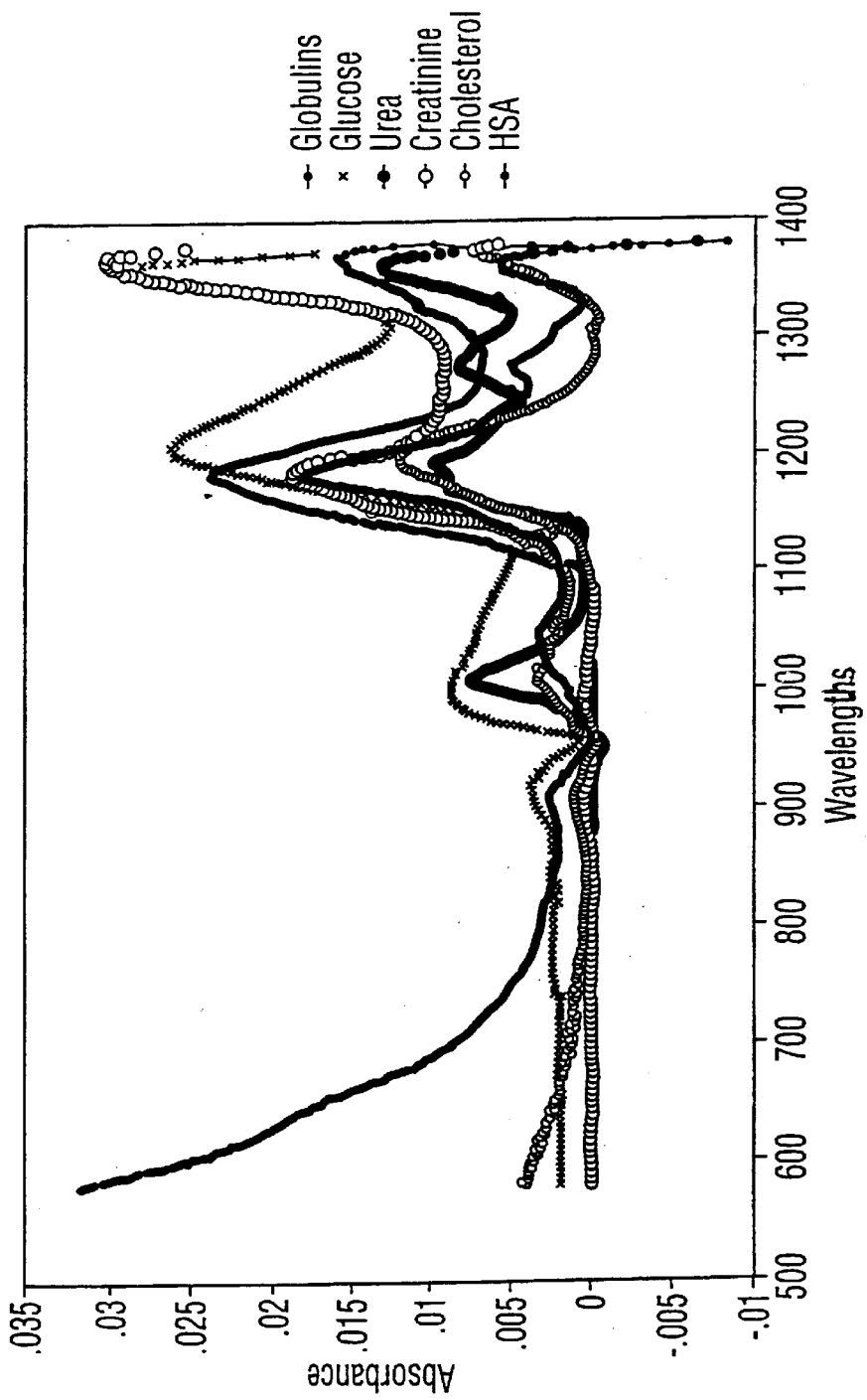
FIG. 1 shows absorbance spectra from 500–1380 nm for globulins, glucose, urea, creatine, cholesterol and human serum albumin with water displacement compensation.

The AV/NIR range has been used because, among other reasons, silicon detectors are sensitive in that range. Silicon detectors, particularly silicon-based detector arrays provide superior noise and dynamic range performance, are readily available, and, are relatively inexpensive. However, the 900 to 1700 nm and further IR wavelength ranges provide sharper spectra for many of the analytes of interest as may be seen by referring to FIG. 1. An Indium Gallium Arsenite (InGaAs) detector may be used to measure spectra in this region while other detectors array can cover further IR ranges. Unfortunately, these detectors provide inferior noise and dynamic range performance in comparison with silicon, consequently the lower signal to noise ratio offsets some of the advantage of the sharper spectra.

To achieve the advantages of measuring spectra in the IR, one or more arrays of spectra are added to measurements in the AV/ NIR region. The results are significantly better than those achieve with measurements of spectra in either range separately.

The light is delivered to the sample or to the tissue, such as a finger, by a suitable conduit such as fiber optics bundle. The light emerging from the finger is collected and delivered to separate sets of detectors by another conduit such as another fiber optics bundle. As just mentioned, a silicon diode array is used to detect light in the AV/NIR region and an InGaAs photodiode array can be used to detect light in the LWNIR region and other detector arrays in further IR ranges. As used herein, "light", "illumination", "radiation" all refer to the light energy provided by a source which is capable of delivering sufficient radiation of a desired wavelength.

Any device which is capable of delivering radiation in the ranges of the invention may be utilized and are within the scope of the present invention.

As just mentioned the light source can emit light over a very wide band-width including light in adjacent to infrared visible and the near infrared spectrum. According to one embodiment, the light from the light source (or sources) is delivered by any optical means to the sample, which preferably is placed in an appropriate receptor. In particular the light may pass first through a collimator (a collection of lenses that concentrate the light into a narrow parallel beam directed at the receptor). In another embodiment, when a light scattered sample is tested, the light, in the form of a wide divergent light beam, is delivered by a fiber-optics means directly to a sample or to a receptor containing the sample. An appropriate receptor is shaped to receive a measured sample. Such samples may be, for example, a part of subject being measured, for example, a finger or arm of a human. An appropriate receptor may also be a sample holder in a form of any transparent container or, for some applications, in a form of calibrated cuvette with parallel walls. Alternatively, a receptor could be shaped so that the part of the human or animal, onto which the light is to be directed, is placed near the receptor rather than within the receptor. Further, an integrating cavity may play the role of sample receptor with light coupled into the cavity either directly or by any optical means including optical fibers. After interaction of the light with the sample, the light is collected by any optical means. The light from the sample can be light that has passed through the sample (body part or tissue, for example) or has reflected off it, or a combination thereof. Preferably, the collected light is light that has passed through the sample.

The collected light is divided into a required number of light beams and each of them is directed to a separate spectral analyzing system, preferably an array-based spectrophotometer. Before entering a spectrometer, each light beam may be optionally shaped to a narrow light source by means of suitably distributed fibers or a set of optical elements and a slit. The light from a narrow light source can be either collimated or directly delivered to a diffraction means.

Radiation from a sample interacts with a dispersion means, such as a grating, which disperses the radiation into its component wavelengths so that the light in the AV/NIR region falls along detectors, preferably a length of linear array of silicon of detectors such that light from the LWNIR and other IR regions falls onto the array of detectors, preferably InGaAs detectors. As is readily understood by those skilled in the art, these arrays are comprised of individual detectors and are sensitive in a range of wavelengths which correspond to the AV and IR regions. Preferably, although not necessarily, all detectors are electronically simultaneously scanned to measure signal registered by each individual unit.

The results from the detector are directed to a microprocessor for analysis of the measurements from the detectors and ultimately produces a concentration result for each constituent by applying one of many known chemometric methods such as form example PLS or PCR. The results can be shown on a display and/or printed on a printer. A keyboard allows a user to control the device, for example, to specify a particular constituent to be measured. The timing and control may be activated by the microprocessor to control the device, for example, to determine number and timing of measurements.

The light source or sources can be a quartz-halogen or a tungsten-halogen bulb, supported by any other light source such as a laser or light emitting diodes (LED) (or other light sources able to emit radiation in the required ranges of AV and IR). Any such source is (or are) powered by a stabilized power source, for example, a DC power supply, or by a battery. Preferably, each linear array detector has a sufficient number of photosensitive elements to cover a required spectral range to provide adequate spectral resolution.

A standard measurement procedure comprises taking reference measurements of incident light (being the light generated in the device when no part of the subject is in contact with the receptor) and taking measurements while the sample is present in the receptor. The negative logarithm of the ratio of sample measurement to reference measurements is then calculated and compared to reference measurements.

Although it should not be construed as a limitation on the method of the invention, the second derivative of measurements may be taken in order to reduce any variation in the result that will be caused by a change in path length for the light.

The noise level within the device may be reduced by a multiple scanning technique whereby the detectors take a number of measurements and then average the results. Preferably, the linear array detector and IR detectors are scanned many times for several repetitions and then the results averaged.

While measuring glucose concentrations is a preferred embodiment of the present invention, the device and method can be used to measure concentration levels of various other constituents found within the blood of humans and animals, for example, amino acids, nitrogen, blood oxygenation, carbon dioxide, cortisol, creatine, creatinine, glucose, ketones, lipids, fat, urea, amino acids, fatty acids, glycosylated hemoglobin, cholesterol, alcohol, lactate, Ca++, K+, Cl-m HCO- and HPO4-, to name a few. Indeed, as will be apparent to those skilled in the art, the method and device can be modified to measure several constituents simultaneously, finally it can be also modified to measure chemical composition of any other materials or samples whose properties may vary in time, demonstrating specific spectral features in AV and IR ranges.

The following is a non-limiting exemplary embodiment of the present invention.

Exemplary Embodiment of Invention

Figure 2:
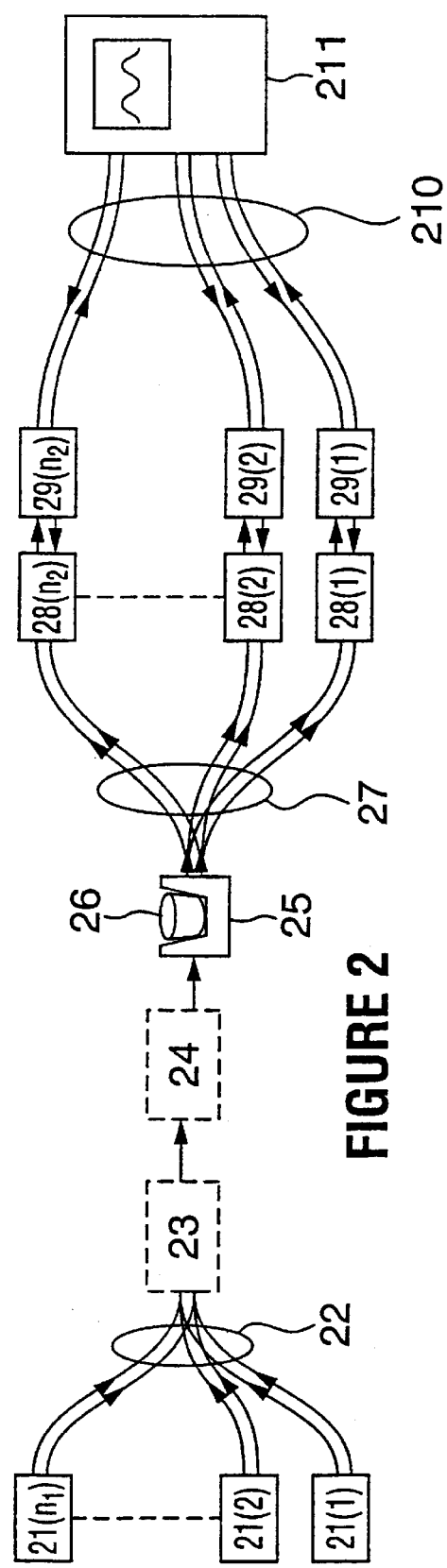
FIG. 2 presents a general concept for simultaneous collection of spectra in a wide spectral range by many array-based instruments, each of which covers a separate spectral range.

Referring now to FIG. 2, a certain number (n1) of light sources 21 generate a broad spectrum of light covering all required spectral ranges. The light sources contain power supplies, light sources, means to collect light from these sources and means to concentrate light into optical elements predestined to nix light from these sources and bring it to the sample.

Light from the light source is collected by light collecting means, preferably by multiple fiber bundles 22, and is optionally delivered through a light mixing device 23 (glass rod, for example) and, optionally a light forming device 24 (light collimator, or focusing lens, for example) to a sample receptor 25 (sample holder, finger holder, integrating cavity or any other device to hold sample) containing a sample 26 (human finger, for example). After interaction with sample the light is collected by a light collecting device 27 (another light bundle, or any other light collecting optical system, lens, for example) and is divided into as many parts as required to cover all possible spectral bands. Division can be performed either by simple splitting of fibers into multiplicity of fiber optics legs or using wide-band or dichroic beam splitters.

Each "part" of light is directed to separate spectrum analyzing devices 28, preferably array-based spectrometers. The number (n2) of spectrometers (generally different from the number of light sources) is selected to cover an entire spectral range of interest for a tested sample with demanded resolution.

The light delivering means together with the spectrum analyzing device may optionally contain a light beam forming optical system, specific for a given spectrum analyzing device, spectrum specific dispersing or light filtering element, a light beam forming system for dispersed light and a wavelength specific array of the photodetectors.

The signal from each array is read by one or more specialized electronics boards (29), usually specific for each kind of array or detector, and in addition to collection of the signal, performs control of the array by providing proper electrical signals. By means of electrical cables 210 boards are connected to a computer 211 which "supervises" the action of the boards, takes information from the boards, stores it and processes using one of many available chemometric methods (for example PLS or PCR) to convert information collected from arrays into information concerning the chemical composition of the tested sample and to present it to user in required form (graphs or any other signal). It is important to appreciate that number $n_1$ and kind of light sources is selected to provide illumination in all spectral bands of the interest in both AV and IR ranges, and in general can be different from number $n_2$ of the spectrum analyzing devices (spectrometers, for example) selected to secure detection in these spectral bands with required resolution.

While the present invention has been described with reference to what are presently considered to be preferred examples, it is to be understood that the invention is not limited to the disclosed examples. To the contrary, the invention is intended to cover various modifications and equivalents included within the spirit and scope of the appended claims.

All publications, patents and patent applications referred to herein are incorporated by reference in their entirety to the same extent as if each individual publication, patent or patent application was specifically and individually indicated to be incorporated by reference in its entirety.

We claim:

1. A method for determining a concentration of a constituent in a sample comprising the steps of:
   i) irradiating the sample with a broad spectrum of radiation from the adjacent visible and near infrared (AV/NIR) region from a first source of radiation;
   ii) collecting radiation after the broad spectrum of radiation from the first source has been directed onto the sample, wherein the collected radiation comprises a broad spectrum of radiation between 500 and 1100 nm;
   iii) dispersing the collected radiation into a dispersed spectrum of component wavelengths onto a detector of AV/NIR radiation, the detector of AV/NIR radiation taking measurements of one or both of transmitted or reflected radiation from the collected radiation, wherein the first source of radiation is approximately oppositely disposed to the detector of AV/NIR radiation;
   iv) transferring the measurements from step iii) to a processor;
   v) irradiating the sample with a broad spectrum of radiation in the longer wavelength near infrared (LWNIR) region from a second source of radiation;
   vi) detecting with a detector of LWNIR radiation a band of radiation in the LWNIR region after the broad spectrum of radiation from the second source has been directed onto the sample, the detector of LWNIR radiation taking measurements of one or both of transmitted and reflected radiation, wherein the band of radiation in the LWNIR region is between 1590 and 1700 nm, and wherein the second source of radiation is approximately oppositely disposed to the detector of LWNIR radiation, and
   vii) transferring the measurements from step vi) to a processor, wherein the processor calculates the concentration of said constituent in said sample from the measurements obtained in steps iii) and vi) using one, or more than one calibration algorithm.

2. A method according to claim 1 wherein the detector of the AV/NIR is one or more spectral instruments with an array of silicon detectors and the detector of LWNIR is one or more spectral instruments with a separate array of infrared sensitive detectors for each band of radiation.

3. A method according to claim 1 wherein the infrared sensitive detectors are InGaAs detectors.

4. A method according to claim 2 wherein the spectral instruments with silicon detectors arrays register light in the all of the visible, visible/infrared and adjacent to visible infrared ranges within the spectral sensitivity range of the detectors.

5. A method according to claim 2 wherein the spectral instruments with infrared sensitive detectors register light in the separate infrared ranges within their spectral sensitivity range.

6. A method according to claim 1 wherein the detector of the AV/NIR is one or more spectral instruments with an array of silicon detectors and the detector of LWNIR is one or more spectral instruments with an array of infrared sensitive detectors and measurements for each band of radiation are taken from appropriate members of the array of infrared sensitive detectors.

7. A method according to claim 1 wherein all detectors register light in their respectable sensitivity ranges virtually simultaneously.

8. A method according to claim 1 wherein the sample is a finger of a subject.

9. A method for determining a concentration of a constituent in a sample comprising the steps of:
   i) irradiating the sample with a broad spectrum of radiation from the adjacent visible and near infrared (AV/NIR) region from a first source of radiation;
   ii) collecting radiation after the broad spectrum of radiation from the first source has been directed onto the sample, wherein the collected radiation comprises a broad spectrum of radiation between 500 and 1100 nm;
   iii) dispersing the collected radiation into a dispersed spectrum of component wavelengths onto a detector of AV/NIR radiation, the detector of AV/NIR radiation taking measurements of one or both of transmitted and reflected radiation from the collected radiation, wherein the first source of radiation is approximately oppositely disposed to the detector of AV/NIR radiation;
   iv) transferring the measurements from step iii) to a processor;
   v) irradiating the sample with one, or more than one band of radiation in the longer wavelength near infrared (LWNIR) region from a second source of radiation;
   vi) detecting with a detector of LWNIR radiation a first and a second band of radiation in the LWNIR region after the broad spectrum of radiation from the second source has been directed onto the sample, the detector of LWNIR radiation taking measurements of one or both of transmitted and reflected radiation, wherein the first band of radiation is between 1100 to 1300 nm and the second band of radiation is between 1590 and 1700 nm, and wherein the second source of radiation is approximately oppositely disposed to the detector of LWNIR radiation, and
   vii) transferring the measurements from step vi) to a processor; wherein the processor calculates the concentration of said constituent in said sample from the measurements obtained in steps iii) and vi) using one, or more than one calibration algorithm.

10. A method according to claim 9 wherein the detector of the AV/NIR is one or more spectral instruments with an array of silicon detectors and the detector of LWNIR is one or more spectral instruments with a separate array of infrared sensitive detectors for each band of radiation.

11. A method according to claim 9 wherein the infrared sensitive detectors are InGaAs detectors.

12. A method according to claim 10 wherein the spectral instruments with silicon detectors arrays register light in the all of the visible, visible/infrared and adjacent to visible infrared ranges within the spectral sensitivity range of the detectors.

13. A method according to claim 10 wherein the spectral instruments with infrared sensitive detectors register light in the separate infrared ranges within their spectral sensitivity range.

14. A method according to claim 9 wherein the detector of the AV/NIR is one or more spectral instruments with an array of silicon detectors and the detector of LWNIR is one or more spectral instruments with an array of infrared sensitive detectors and measurements for each band of radiation are taken from appropriate members of the array of infrared sensitive detectors.

15. A method according to claim 9 wherein all detectors register light in their respectable sensitivity ranges virtually simultaneously.

16. A method according to claim 9 wherein the sample is a finger of a subject.

17. A method for determining a concentration of a constituent in a sample comprising the steps of:
   i) irradiating the sample with a broad spectrum of radiation from the adjacent visible and near infrared (AV/NIR) region from a first source of radiation;
   ii) collecting radiation after the broad spectrum of radiation from the first source has been directed onto the sample, wherein the collected radiation comprises a broad spectrum of radiation between 500 and 1100 nm;
   iii) dispersing the collected radiation into a dispersed spectrum of component wavelengths onto a detector of AV/NIR radiation, the detector of the AV/NIR radiation taking measurements of one or both of transmitted and reflected radiation from the collected radiation, wherein the first source of radiation is approximately oppositely disposed to the detector of AV/NIR radiation;
   iv) transferring the measurements from step iii) to a processor;
   v) irradiating the sample with a broad spectrum of radiation from the LWNIR the longer wavelength near infrared (LWNIR) region from a second source of radiation;
   vi) collecting radiation after the broad spectrum of radiation from the second source has been directed onto the sample, wherein the collected radiation comprises a first band of radiation between 1100 to 1300 nm and a second band of radiation between 1590 and 1700 nm;
   vii) dispersing the collected radiation into dispersed spectra of bands of radiation onto a detector of LWNIR radiation, the detector of LWNIR radiation taking measurements of one or both of transmitted and reflected radiation, wherein the second source of radiation is approximately oppositely disposed to the detector of LWNIR radiation, and
   (viii) transferring the measurements from step vii) to a processor; wherein the processor calculates the concentration of said constituent in said sample from the measurements from steps iii) and vii) and one, or more than one calibration algorithm.

18. A method according to claim 17 wherein the detector of the AV/NIR is one or more spectral instruments with an array of silicon detectors and the detector of LWNIR is one or more spectral instruments with a separate array of infrared sensitive detectors for each band of radiation.

19. A method according to claim 17 wherein the infrared sensitive detectors are InGaAs detectors.

20. A method according to claim 18 wherein the spectral instruments with silicon detectors arrays register light in the all of the visible, visible/infrared and adjacent to visible infrared ranges within the spectral sensitivity range of the detectors.

21. A method according to claim 18 wherein the spectral instruments with infrared sensitive detectors register light in the separate infrared ranges within their spectral sensitivity range.

22. A method according to claim 17 wherein the detector of the AV/NIR is one or more spectral instruments with an array of silicon detectors and the detector of LWNIR is one or more spectral instruments with an array of infrared sensitive detectors and measurements for each band of radiation are taken from appropriate members of the array of infrared sensitive detectors.

23. A method according to claim 17 wherein all detectors register light in their respectable sensitivity ranges virtually simultaneously.

24. A method according to claim 17 wherein the sample is a finger of a subject.

* * * * *

UNITED STATES PATENT AND TRADEMARK OFFICE
CERTIFICATE OF CORRECTION

PATENT NO. : 6,741,875 B1
DATED : May 25, 2004
INVENTOR(S) : Romuald Pawluczyk, Thomas Scecina and Theodore E. Cadell It is certified that error appears in the above-identified patent and that said Letters Patent is hereby corrected as shown below:

<u>Title page,</u>
Item [75], Inventors, delete "Romauld" and substitute therefore -- Romuald --.

Signed and Sealed this

Seventh Day of September, 2004

JON W. DUDAS
*Director of the United States Patent and Trademark Office*

UNITED STATES PATENT AND TRADEMARK OFFICE
CERTIFICATE OF CORRECTION

PATENT NO.  : 6,741,875 B1
DATED       : May 25, 2004
INVENTOR(S) : Romuald Pawluczyk, Thomas Scecina and Theodore E. Cadell It is certified that error appears in the above-identified patent and that said Letters Patent is hereby corrected as shown below:

Column 12,
Lines 36-37, "one or both of transmitted or reflected" should read -- transmitted --.
Lines 49-50, "one or both of transmitted and reflected" should read -- transmitted --.
Line 65, the claim dependency "1" should read -- 2 --.

Column 13,
Lines 2 and 67, "silicon detectors arrays" should read -- an array of silicon detectors --.
Lines 34-35 and 47-48, "one or both of transmitted and reflected" should read
-- transmitted --.
Line 64, the claim dependency "9" should read -- 10 --.

Column 14,
Lines 32-33 and 50, "one or both of transmitted and reflected" should read
-- transmitted --.
Line 64, the claim dependency "17" should read -- 18 --.
Line 67, "silicon detectors arrays" should read -- an array of silicon detectors --.

Signed and Sealed this

Twenty-eighth Day of February, 2006

JON W. DUDAS
*Director of the United States Patent and Trademark Office*